(12) United States Patent
Kawaguchi et al.

(10) Patent No.: US 11,389,752 B2
(45) Date of Patent: Jul. 19, 2022

(54) FILTRATION DEVICE

(71) Applicant: Murata Manufacturing Co., Ltd., Nagaokakyo (JP)

(72) Inventors: Toshikazu Kawaguchi, Nagaokakyo (JP); Takashi Kondo, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 123 days.

(21) Appl. No.: 16/933,064

(22) Filed: Jul. 20, 2020

(65) Prior Publication Data

US 2020/0353383 A1 Nov. 12, 2020

Related U.S. Application Data

(63) Continuation of application No. PCT/JP2018/045898, filed on Dec. 13, 2018.

(30) Foreign Application Priority Data

Mar. 19, 2018 (JP) .............................. JP2018-051473

(51) Int. Cl.
*B01D 35/34* (2006.01)
*B01D 29/05* (2006.01)

(52) U.S. Cl.
CPC ............. *B01D 29/05* (2013.01); *B01D 35/34* (2013.01); *B01D 2201/184* (2013.01); *B01D 2201/302* (2013.01)

(58) Field of Classification Search
CPC .. B01D 29/05; B01D 35/34; B01D 2201/184; B01D 36/001; A61M 1/3633; A61M 2205/7545
See application file for complete search history.

(56) References Cited

U.S. PATENT DOCUMENTS 4,683,058 A 7/1987 Lyman et al.
5,167,929 A 12/1992 Korf et al.
(Continued)

FOREIGN PATENT DOCUMENTS

JP S56156858 U * 11/1981
JP S5848350 U 4/1983
(Continued)

OTHER PUBLICATIONS

International Search Report Issued for PCT/JP2018/045898, dated Feb. 26, 2019.

(Continued)

*Primary Examiner* — Waqaas Ali
(74) *Attorney, Agent, or Firm* — ArentFox Schiff LLP (57) ABSTRACT

A filtration device that includes: a filtration filter having a first main surface that captures a filtration target object contained in a liquid and a second main surface that faces the first main surface; and a housing that holds the filtration filter, and defines a liquid inflow path that faces the first main surface and a liquid discharge path that faces the second main surface, the housing including a tubular portion that extends in a direction away from the second main surface of the filtration filter and defines the liquid discharge path, and a flange portion that extends from an outer peripheral surface of the tubular portion, and the flange portion includes a vent hole extending away from the outer peripheral surface of the tubular portion.

13 Claims, 7 Drawing Sheets

(56) References Cited

U.S. PATENT DOCUMENTS

2011/0300609 A1  12/2011  Lim et al.
2017/0120237 A1  5/2017  McCully et al.
2017/0203260 A1  7/2017  Kondo et al.

FOREIGN PATENT DOCUMENTS

| | | |
|---|---|---|
| JP | S62221459 A | 9/1987 |
| JP | 2004317179 A | 11/2004 |
| JP | 3130711 U | 4/2007 |
| JP | 2011525805 A | 9/2011 |
| JP | 2017518767 A | 7/2017 |
| KR | 830000360 B1 * | 3/1983 |

OTHER PUBLICATIONS

Written Opinion of the International Searching Authority issued for PCT/JP2018/045898, dated Feb. 26, 2019.

* cited by examiner

| | VENT-HOLE OPENING AREA S1 (mm²) | THROUGH-HOLE WIDTH d (μm) | THROUGH-HOLE OPENING AREA M (μm²) | THROUGH-HOLE NUMBER N (PIECE) | FILTER OPENING AREA S2 (mm²) | S1/S2 | LIQUID PASSAGE STATE |
|---|---|---|---|---|---|---|---|
| SAMPLE 1 | 6 | 10 | 100 | 5,670,000 | 567 | 1.1% | COMPLETE LIQUID PASSAGE |
| SAMPLE 2 | 24 (6×4PLACE) | 10 | 100 | 5,670,000 | 567 | 4.4% | COMPLETE LIQUID PASSAGE |
| SAMPLE 3 | 6 | 4 | 16 | 14,187,500 | 227 | 2.6% | COMPLETE LIQUID PASSAGE |
| SAMPLE 4 | 8 (2×4PLACE) | 20 | 400 | 220,000 | 88 | 9% (※UPPER LIMIT) | COMPLETE LIQUID PASSAGE |
| SAMPLE 5 | 0.01 | 4 | 16 | 35,437,500 | 567 | 0.0017% | COMPLETE LIQUID PASSAGE |
| SAMPLE 6 | 0.0098 (0.0049×2PLACE) | 2 | 4 | 141,750,000 | 567 | 0.00173% (※LOWER LIMIT) | COMPLETE LIQUID PASSAGE |
| SAMPLE 7 | 0 | 2 | 4 | 141,750,000 | 567 | 0% | PROLONGED TEMPORARILY STOP LIQUID PASSAGE |
| SAMPLE 8 | 0 | 40 | 1,600 | 354,375 | 567 | 0% | COMPLETE LIQUID PASSAGE |
| SAMPLE 9 | 0.0049 LESS THAN | 2 | 4 | 141,750,000 | 567 | 0.0001% | STOP LIQUID PASSAGE |
| SAMPLE 10 | 24 (6×4PLACE) | 1 | 1 | 567,000,000 | 567 | 4.4% | STOP LIQUID PASSAGE |
| SAMPLE 11 | 56.7 | 20 | 400 | 1,417,500 | 567 | 10% | COMPLETE LIQUID PASSAGE LIQUID SCATTER |

FILTRATION DEVICE

CROSS REFERENCE TO RELATED APPLICATIONS

The present application is a continuation of International application No. PCT/JP2018/045898, filed Dec. 13, 2018, which claims priority to Japanese Patent Application No. 2018-051473, filed Mar. 19, 2018, the entire contents of each of which are incorporated herein by reference.

FIELD OF THE INVENTION

The present invention relates to a filtration device for filtering a filtration target object contained in a liquid.

BACKGROUND OF THE INVENTION

As an existing filtration device of this type, for example, a filtration device described in Patent Document 1 has been known. Patent Document 1 discloses a filtration device including a filtration filter for filtering blood that is a liquid containing a filtration target object such as a thrombus.

Patent Document 1: Japanese Utility Model Registration No. 3130711

SUMMARY OF INVENTION

However, in the existing filtration device, when the filtration device is disposed so as to cover an upper cavity of a bottomed tubular container, such as a centrifuge tube, and a liquid that has passed through the filtration filter is contained in the container, there is an issue that filtration efficiency of the filtration target object may be reduced.

An object of the present invention is to solve the problem described above and to provide a filtration device capable of suppressing a decrease in filtration efficiency of a filtration target object.

In order to achieve the above object, a filtration device according to an aspect of the present invention includes: a filtration filter having a first main surface that captures a filtration target object contained in a liquid and a second main surface that faces the first main surface; and a housing that holds the filtration filter, and defines a liquid inflow path that faces the first main surface and a liquid discharge path that faces the second main surface, the housing including: a tubular portion that extends in a direction away from the second main surface of the filtration filter and defines at least a part of the liquid discharge path; and a flange portion that extends from an outer peripheral surface of the tubular portion the flange portion including at least one vent hole extending away from the outer peripheral surface of the tubular portion.

According to the present invention, it is possible to provide a filtration device capable of suppressing a decrease in filtration efficiency of a filtration target object.

DETAILED DESCRIPTION OF THE PREFERRED EMBODIMENTS (Underlying Findings of Present Invention)

The present inventors have conducted intensive studies in order to suppress a decrease in filtration efficiency of a filtration target object, and as a result, have obtained the following findings.

In a case where filtering a filtration target object such as a thrombus from blood, a plurality of through-holes included in a filtration filter are required to be extremely small holes of a size of equal to or less than several 10 µm. The present inventors have found that when the filtration device is disposed so as to cover an upper cavity of a container and a liquid that has passed through the filtration filter is contained in the container, the plurality of through-holes are blocked with the liquid, pressure in the container is increased, and the liquid is less likely to flow into the container. In this case, flow of the liquid is inhibited, and thus the filtration efficiency of the filtration target object is reduced.

In addition, the present inventors have found that as the pressure in the container is increased, gas (air) in the container may be mixed into the liquid as bubbles and reach a main surface of the filtration filter. For example, in a case where the filtration target object is a cell, when the cell is exposed to gas in the bubble, a cell activity may be reduced.

As a result of intensive studies, the present inventors have found a configuration in which a tubular portion defining a liquid discharge path is provided in a housing containing the filtration filter, and a gap is formed between the tubular portion and the container. Further, the present inventors have found a configuration in which a flange portion mounted on an opening end portion of the container is provided on an outer peripheral surface of the housing, and a communication hole for communicating the gap and an outside space is provided in the flange portion. According to this configuration, the gas in the container is exhausted to the outside space through the communication hole, and the increase in the pressure in the container can be suppressed. Further, the tubular portion separates a flow path through which the liquid flows and a flow path through which the gas flows, and it is possible to suppress mixing of the gas into the liquid. As a result, it is possible to suppress a decrease in the filtration efficiency of the filtration target object.

In view of these points, the present inventors have arrived at the following invention.

A filtration device according to one aspect of the present invention includes: a filtration filter having a first main surface that captures a filtration target object contained in a liquid and a second main surface that faces the first main surface; and a housing that holds the filtration filter, and defines a liquid inflow path that faces the first main surface and a liquid discharge path that faces the second main surface, the housing including: a tubular portion that extends in a direction away from the second main surface of the filtration filter and defines at least a part of the liquid discharge path; and a flange portion that extends from an outer peripheral surface of the tubular portion, the flange portion including at least one vent hole extending away from the outer peripheral surface of the tubular portion.

According to this configuration, the gas in the container is exhausted to the outside space through the vent hole provided in the flange portion, and it is possible to suppress the increase in the pressure in the container. Further, the tubular portion separates the flow path through which the liquid flows and the flow path through which the gas flows, and it is possible to suppress the mixing of the gas into the liquid. As a result, it is possible to suppress a decrease in the filtration efficiency of the filtration target object.

Note that the vent hole may be configured as a groove that extends to an outer side portion along a lower surface of the flange portion. According to this configuration, it is possible to bend a flow of gas flowing through the gap along the lower surface of the flange portion. That is, the flow of gas exhausted from the inside of the container to the outside space can be inhibited (decelerated) by the flange portion. Accordingly, for example, the gas in the container is exhausted to the outside space at once, whereby it is possible to prevent the liquid discharged into the container from being discharged to the outside space together with the gas.

Further, in the flange portion, a plurality of the vent holes may be provided at intervals, and a communication hole that allows the plurality of vent holes to communicate with each other may be provided. According to this configuration, for example, even in a case where any one of the plurality of vent holes is clogged with foreign matters, it is possible to flow the gas into the other vent holes through the communication hole and to exhaust the gas from the other vent holes to the outside space. As a result, it is possible to more reliably suppress a decrease in the filtration efficiency of the filtration target object.

Further, the flange portion may be provided with a plurality of the vent holes at equal or substantially equal intervals. According to this configuration, for example, even in a case where the tubular portion is unevenly disposed in a manner such that the gap is non-uniform with respect to the opening end portion of the container, and the gap connected to any one vent hole is closed, gas can be exhausted to the outside space through the other vent holes. As a result, it is possible to more reliably suppress a decrease in the filtration efficiency of the filtration target object.

Further, the filtration filter may have a plurality of through-holes penetrating from the first main surface to the second main surface, an opening area of each of the plurality of through-holes may be 4 $\mu m^2$ to 400 $\mu m^2$, an opening area (S1) of the vent hole may be equal to or more than 0.0049 $mm^2$, and a ratio (S1/S2) of the opening area (S1) of the vent hole to an opening area (S2) of the filtration filter may be equal to or more than 0.00173%. According to this configuration, it is possible to prevent the vent hole from becoming excessively small, and to exhaust the gas in the container through the vent hole to the outside space more reliably. As a result, it is possible to more reliably suppress a decrease in the filtration efficiency of the filtration target object. Note that the "opening area of the vent hole" refers to a minimum opening area of the vent hole when one vent hole is provided, and refers to a total opening area obtained by adding the minimum opening area of each vent hole when a plurality of vent holes is provided.

In addition, the ratio (S1/S2) of the opening area (S1) of the vent hole to the opening area (S2) of the filtration filter may be equal to or less than 9.0%. According to this configuration, it is possible to suppress an excessive increase in the vent hole, and it is possible to prevent dust or the like from entering through the vent hole. Further, the gas in the container is exhausted to the outside space at once, whereby it is possible to prevent the liquid discharged into the container from being discharged to the outside space together with the gas.

In addition, the housing may be made of resin. According to this configuration, it is possible to reduce a weight as compared with a case where the housing is made of a metal such as lead. Thereby, it is possible to increase the extent of the use thereof. Note that, even when the housing is made of resin and the weight is reduced, according to the above configuration, the gas in the container can be exhausted through the vent hole, and thus, for example, it is possible to prevent the filtration device from being detached from the container due to an increase in the pressure in the container.

In addition, the housing may include a first housing portion that defines the liquid inflow path, and a second housing portion that includes the tubular portion, and the first housing portion and the second housing portion may be configured to fit with each other and hold the filtration filter therebetween. According to this configuration, it is possible to facilitate easy manufacture of the filtration device.

In addition, the filtration filter may be held in a position above the vent hole relative to the liquid inflow path. According to this configuration, it is possible to prevent the liquid that has passed through the filtration filter from overflowing from the inside of the container and flowing back to the filtration filter.

Hereinafter, an embodiment of the present invention will be described with reference to the accompanying drawings. Note that, in each drawing, each element is shown exaggeratingly for ease of description.

Further, in the following description, for convenience of description, terms indicating directions such as "upper", "lower", and "oblique" are used assuming a state in normal use. However, these terms are not meant to limit the usage state and the like of the filtration device according to the present invention.

Embodiment

Figure 1:
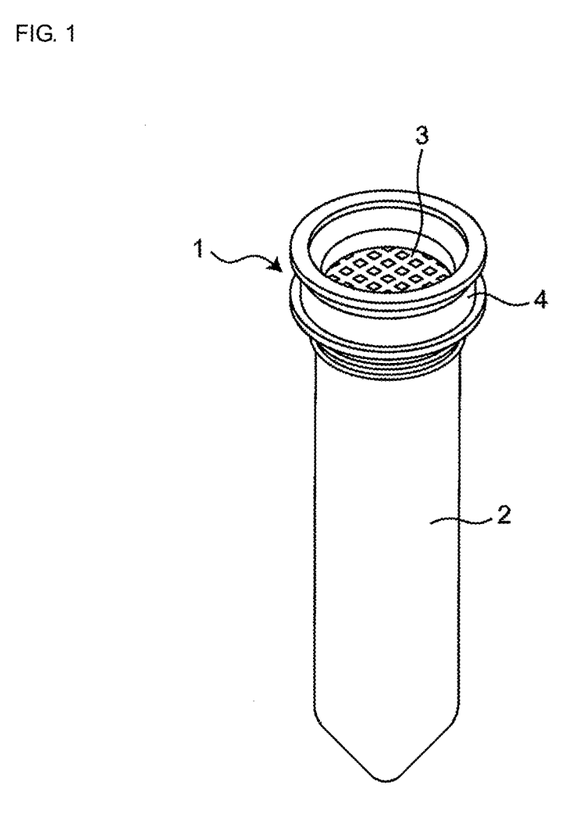
FIG. 1 is a perspective view illustrating a state in which a filtration device according to an embodiment of the present invention is disposed so as to cover an upper cavity of a bottomed tubular container.
Figure 2:
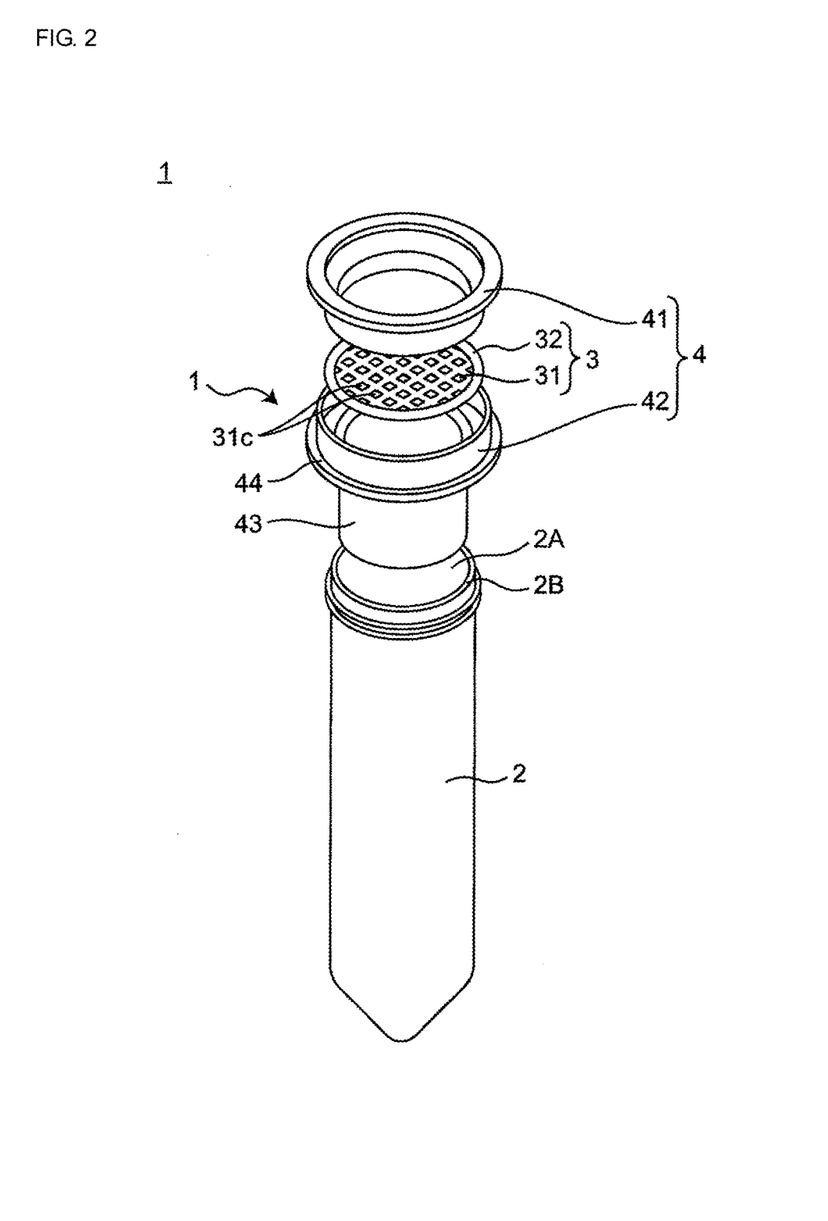
FIG. 2 is an exploded perspective view of FIG. 1.
Figure 3:
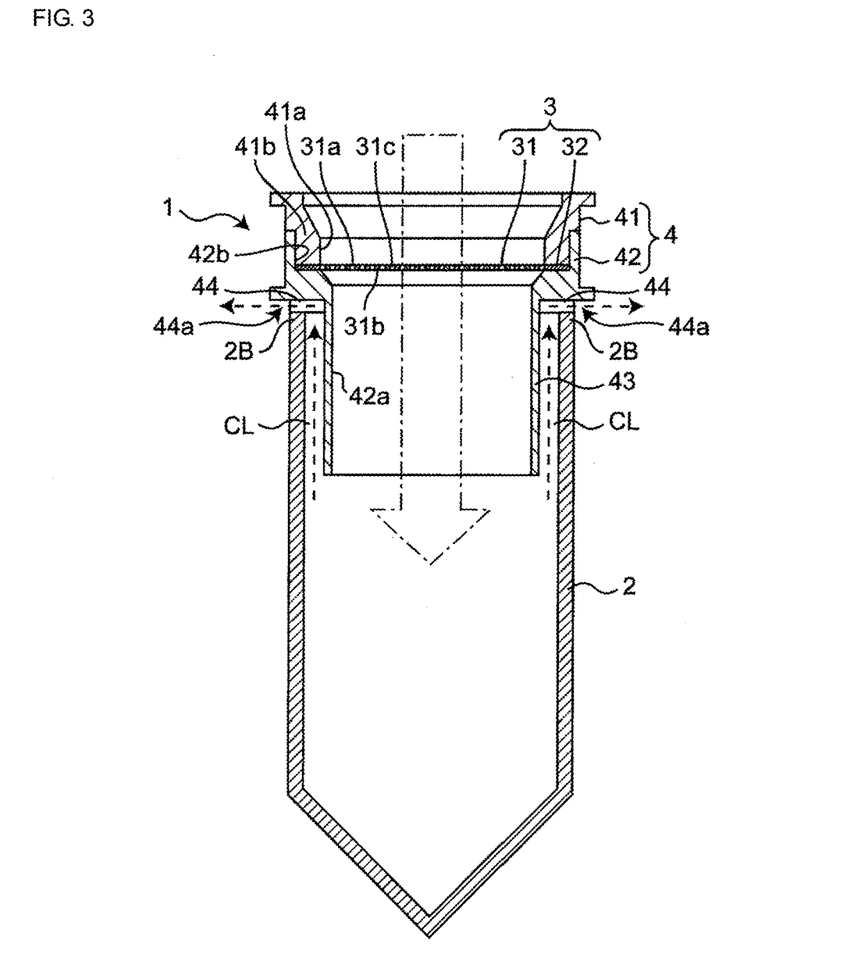
FIG. 3 is a longitudinal sectional view of FIG. 1.
Figure 4:
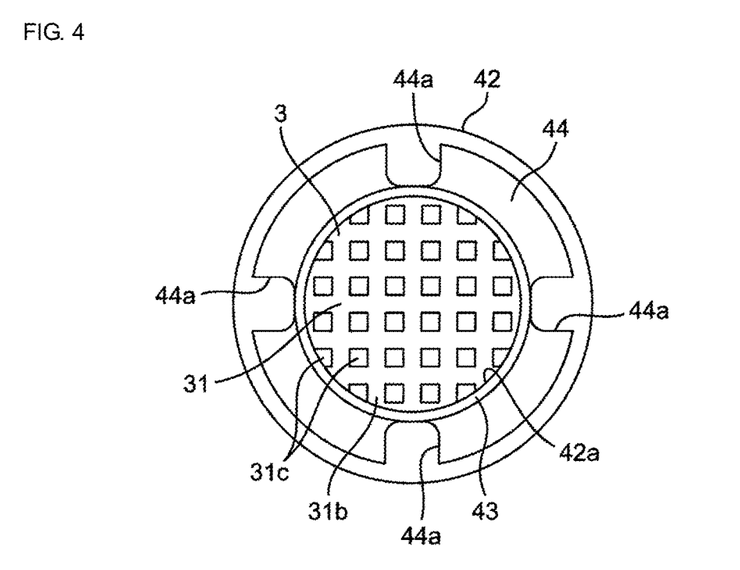
FIG. 4 is a bottom view of the filtration device illustrated in FIG. 1.
Figure 5:
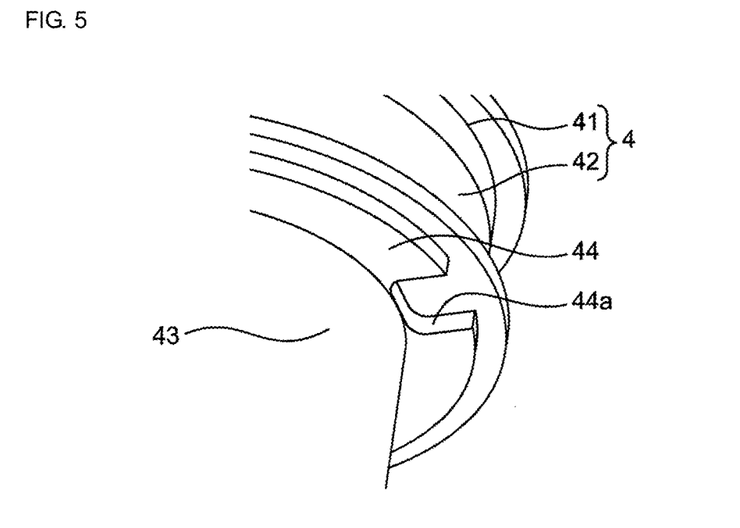
FIG. 5 is a partially enlarged perspective view of the filtration device illustrated in FIG. 1 as viewed obliquely from below.

A configuration of a filtration device according to the present embodiment will be described. FIG. 1 is a perspective view illustrating a state in which the filtration device according to the embodiment of the present invention is disposed so as to cover an upper cavity of a bottomed tubular container. FIG. 2 is an exploded perspective view of FIG. 1. FIG. 3 is a longitudinal sectional view of FIG. 1. FIG. 4 is a bottom view of the filtration device illustrated in FIG. 1. FIG. 5 is a partially enlarged perspective view of the filtration device illustrated in FIG. 1 as viewed obliquely from below.

As illustrated in FIG. 1 to FIG. 3, a filtration device 1 according to the present embodiment is disposed so as to cover an upper cavity 2A of a bottomed tubular container 2, such as a centrifuge tube. As illustrated in FIG. 3, in a state in which the filtration device 1 is disposed so as to cover the upper cavity 2A of the container 2, a liquid containing a filtration target object is flowed so as to be contained in the container 2 through the filtration device 1, so that the filtration target object is filtered out of the liquid by the filtration device 1. Note that the "bottom" of the "bottomed tubular shape" is not limited to a flat surface, and includes, for example, an inclined surface as illustrated in FIG. 2. In addition, the "tube" of the "bottomed tubular shape" is not limited to a cylinder, and includes, for example, a tube that is oval or rectangular in cross-section.

In the present embodiment, the "filtration target object" refers to a target object to be filtered out of target objects contained in the liquid. For example, the filtration target object may be biological products contained in the liquid. The term "biological product" means a substance derived from an organism, such as cells (eukaryote), bacteria (eubacteria), virus and the like. Examples of cells (eukaryotes) include, for example, induced pluripotent stem cells (iPS cells), ES cells, stem cells, mesenchymal stem cells, mononuclear cells, single cells, cell clusters, floating cells, adherent cells, nerve cells, leukocyte, cells for regenerative medicine, autologous cells, cancer cells, circulating tumor cells (CTC) in blood, HL-60, HELA, and fungi. Examples of bacteria (eubacteria) include, for example, *E. coli, Mycobacterium tuberculosis*.

The filtration device 1 includes a filtration filter 3 and a housing 4 that is configured to include the filtration filter 3.

As illustrated in FIG. 2 and FIG. 3, the filtration filter 3 includes a filter portion 31 and a frame portion 32 disposed so as to surround an outer peripheral portion of the filter portion 31. In the present embodiment, the filtration filter 3 is a metal filter.

The filter portion 31 is a thin plate-shaped or film-shaped structure having a first main surface 31a that captures a filtration target object contained in the liquid and a second main surface 31b that faces the first main surface 31a. In the present embodiment, the filter portion 31 is a metal porous film. The filter portion 31 is provided with a plurality of through-holes 31c penetrating from the first main surface 31a to the second main surface 31b.

The filter portion 31 has, for example, a circular shape, a rectangular shape, or an oval shape when viewed from a thickness direction of the filtration filter 3. In the present embodiment, the filter portion 31 has a substantially circular shape. Note that, in the present specification, the term "substantially circular shape" means that a ratio of a length of a major axis to a length of a minor axis is 1.0 to 1.2.

The plurality of through-holes 31c are periodically disposed on the first main surface 31a and the second main surface 31b of the filter portion 31. In the present embodiment, the plurality of through-holes 31c are provided at equal intervals in a matrix in the filter portion 31.

In the present embodiment, the shape of the through-holes 31c are square when viewed from the first main surface 31a side of the filter portion 31. Note that the shape of the through-holes 31c are not limited to a square shape, and may be another shape, for example, a rectangular shape, a circular shape, an oval shape, or the like.

Further, in the present embodiment, the shape (cross-sectional shape) of the through-holes 31c in the cross-section cut in the thickness direction of the filter portion 31 have a rectangular shape. Specifically, the cross-sectional shape of the through-holes 31c are a rectangular shape in which a length of one side in a radius direction of the filtration filter 3 is longer than a length of one side in the thickness direction of the filtration filter 3. Note that the cross-sectional shape of the through-holes 31c are not limited to a rectangular shape, and may be, for example, a tapered shape such as a parallelogram shape or a trapezoidal shape, a symmetrical shape, or an asymmetrical shape.

Further, in the present embodiment, the plurality of through-holes 31c are provided at equal intervals in two arrangement directions parallel to each side of the square when viewed from the first main surface 31a side of the filter portion 31. That is, the plurality of through-holes 31c are provided in a square lattice arrangement. According to this configuration, it is possible to increase an aperture ratio of the filtration filter 3, and it is possible to reduce a passage resistance of the liquid with respect to the filtration filter 3. Further, it is possible to shorten the time of the filtration and reduce the stress on the filtration target object.

Note that the arrangement of the plurality of through-holes 31c is not limited to the square lattice arrangement, and may be, for example, a quasi-periodic arrangement or a periodic arrangement. As long as the arrangement is a square arrangement, the periodic arrangement, as an example, may be a rectangular arrangement in which intervals in two arrangement directions are not equal to each other, and may be a triangular lattice arrangement, a regular triangular lattice arrangement, or the like. Note that the plurality of through-holes 31c are only required to be provided in the filter portion 31, and the arrangement is not limited.

The interval between the plurality of through-holes 31c is appropriately designed in accordance with the type (size, form, property, elasticity) or an amount of the filtration target object. Here, the interval between the through-holes 31c means a distance between a center of an arbitrary through-hole 31c and a center of an adjacent through-hole 31c when the through-hole 31c is viewed from the first main surface 31a side of the filter portion 31. In the case of the structure of the periodic arrangement, the interval between the through-holes 31c is, for example, greater than one time and equal to or less than 10 times one side of the through-hole 31c, and is preferably equal to or less than three times one side of the through-hole 31c. Further, for example, the aperture ratio of the filter portion 31 is equal to or more than 10%, and preferably equal to or more than 25%. According to this configuration, it is possible to reduce the passage resistance of the liquid with respect to the filter portion 31. As a result, a processing time can be shortened, and the stress on the filtration target object can be reduced. Note that the aperture ratio is calculated by (an area occupied by the through-hole 31c)/(a projection area of the first main surface 31a when the through-hole 31c is assumed not to be provided).

The thickness of the filter portion 31 is preferably greater than 0.1 times and equal to or less than 100 times the size of the through-hole 31c. More preferably, the thickness of the filter portion 31 is greater than 0.5 times and equal to or less than 10 times the size of the through-hole 31c. According to this configuration, it is possible to reduce the resistance of the filtration filter 3 with respect to the liquid, and it is possible to shorten the time of the filtration. As a result, it is possible to reduce the stress on the filtration target object.

In the filter portion 31, it is preferable that the first main surface 31a with which the liquid containing the filtration target object is in contact have a small surface roughness. Here, the surface roughness means an average value of a difference between a maximum value and a minimum value measured by a stylus-type step meter at arbitrary five points on the first main surface 31a. In the present embodiment, the surface roughness is preferably smaller than the size of the filtration target object, and is more preferably smaller than half of the size of the filtration target object. According to this configuration, an adhesion of the filtration target object to the first main surface 31a of the filter portion 31 is reduced, and the resistance of the liquid can be reduced.

A material of the filter portion 31 contains a metal and/or a metal oxide as a main component thereof. The filter portion 31 may be, for example, gold, silver, copper, platinum, nickel, palladium, an alloy thereof, and an oxide thereof.

The frame portion 32 is a member disposed so as to surround the outer peripheral portion of the filter portion 31. The frame portion 32 is formed in a ring shape as viewed from the first main surface 31a side of the filter portion 31. Further, when the filtration filter 3 is viewed from the first main surface 31a side, a center of the frame portion 32 coincides with a center of the filter portion 31. That is, the frame portion 32 is formed on a concentric circle with the filter portion 31.

In the present embodiment, the frame portion 32 is formed to have a thickness larger than a film thickness of the filter portion 31. According to this configuration, it is possible to increase the mechanical strength of the filtration filter 3. The frame portion 32 is formed to have a rectangular cross-section. The frame portion 32 functions as a connection portion that connects the filtration filter 3 and the housing 4. In the present embodiment, a material of the frame portion 32 is the same as the material of the filter portion 31.

In the present embodiment, the filtration filter 3 has a diameter of 33 mm, the filter portion 31 has a diameter of 28 mm, and the frame portion 32 has a width of 2.5 mm. In addition, the thickness of the filter portion 31 is about 10 μm, and the thickness of the frame portion 32 is 15 μm. The various dimensions of the filtration filter 3 are not limited to these, and may be other dimensions.

The housing 4 includes a first housing portion 41 and a second housing portion 42. The first housing portion 41 and the second housing portion 42 are configured to fit with each other and hold the frame portion 32, which is an outer peripheral portion of the filtration filter 3, therebetween. In the present embodiment, the first housing portion 41 and the second housing portion 42 fit with each other so that the frame portion 32 of the filtration filter 3 is sandwiched between a convex step portion 41b and a concave step portion 42b. Accordingly, a portion of the frame portion 32 held by the first housing portion 41 and the second housing portion 42 is not bent.

The first housing portion 41 is a tubular member made of resin. Inside the first housing portion 41, a liquid inflow path 41a is defined so as to face the first main surface 31a of the filter portion 31. The liquid inflow path 41a is a flow path through which the liquid including the filtration target object flows when the filtration is performed. In the present embodiment, the liquid inflow path 41a is a cylindrical flow path, and is formed so that a diameter gradually decreases as approaching the filter portion 31.

The second housing portion 42 is a tubular member made of resin. Inside the second housing portion 42, a liquid discharge path 42a is defined that faces the second main surface 31b of the filter portion 31. The liquid discharge path 42a is a flow path for discharging the liquid that has passed through the filtration filter 3. In the present embodiment, the liquid discharge path 42a is a cylindrical flow path. As indicated by dashed-dotted line arrows in FIG. 3, the liquid containing the filtration target object is supplied to the filtration filter 3 through the liquid inflow path 41a, in which the filtration target object is filtered by the filtration filter 3, and the liquid is discharged to the outside of the filtration device 1 through the liquid discharge path 42a. The liquid discharged through the liquid discharge path 42a is contained in the container 2.

The second housing portion 42 includes a tubular portion 43 and a flange portion 44.

The tubular portion 43 is a portion that extends in a direction away from the second main surface 31b of the filter portion 31 and defines at least a portion of the liquid discharge path 42a. In the present embodiment, the tubular portion 43 is formed in a cylindrical shape. When the filtration device 1 is disposed so as to cover the upper cavity 2A of the container 2, as illustrated in FIG. 3, the tubular portion 43 forms a gap CL in an inner side portion with respect to an opening end portion 2B of the upper cavity 2A of the container 2. That is, an outer diameter of the tubular portion 43 is set to be smaller than an inner diameter of the opening end portion 2B of the container 2.

The flange portion 44 is configured to extend outwardly from an outer peripheral surface of the tubular portion 43. In the present embodiment, the flange portion 44 is configured to extend outwardly from an upper end portion of the outer peripheral surface of the tubular portion 43. An angle formed by the tubular portion 43 and the flange portion 44 is, for example, a right angle or a substantially right angle. The outer shape of the flange portion 44 is preferably a circular shape. When the filtration device 1 is disposed so as to cover the upper cavity 2A of the container 2, the flange portion 44 rests on the opening end portion 2B of the container 2. That is, an outer diameter of the flange portion 44 is set to be larger than the inner diameter of the opening end portion 2B of the container 2.

The flange portion 44 is provided with at least one vent hole 44a for communicating the gap CL with the outside space when placed on the opening end portion 2B of the container 2. In the present embodiment, as illustrated in FIG. 4, four vent holes 44a are provided at equal intervals. Note that the four vent holes 44a are not limited to being provided at exactly equal intervals, and may be provided at substantially equal intervals.

In the present embodiment, as illustrated in FIG. 4 and FIG. 5, the vent holes 44a are formed by grooves that extend to the outer side portion along the lower surface of the flange portion 44. When the liquid that has passed through the filtration device 1 is contained in the container 2, gas (e.g., air) in the container 2 is exhausted to the outside space through the gap CL and the vent hole 44a, as indicated by a dotted line arrow in FIG. 3.

According to the filtration device 1 according to the present embodiment, the gas in the container 2 can be exhausted to the outside space through the vent hole 44a provided in the flange portion 44, and thus pressure in the container 2 can be prevented from rising due to the liquid that has passed through the filtration device 1.

Further, according to the filtration device 1 according to the present embodiment, the tubular portion 43 functions so as to separate the liquid discharge path 42a serving as a flow path through which the liquid flows and the gap CL serving as a flow path through which the gas flows, so that it is possible to suppress mixing of the gas into the liquid. As a result, it is possible to suppress a decrease in the filtration efficiency of the filtration target object. Note that, in a case where a cavity is provided on the outer peripheral surface of the tubular portion 43, the gas flowing through the gap CL may enter into the fluid discharge path 42a through the cavity, and may be mixed into the liquid flowing in the liquid discharge path 42a. In this case, the effect of suppressing the decrease in the filtration efficiency of the filtration target object is reduced. Therefore, as in the filtration device 1 according to the present embodiment, it is preferable that the cavity not be provided on the outer peripheral surface of the tubular portion 43.

Further, according to the filtration device 1 according to the present embodiment, since the vent holes 44a are configured as grooves that extend to the outer side portion along the lower surface of the flange portion 44, it is possible to bend the flow of gas flowing through the gap CL along the lower surface of the flange portion 44. That is, the flow of gas exhausted from the inside of the container 2 to the outside space can be inhibited (decelerated) by the flange portion 44. Accordingly, for example, the gas in the container 2 is exhausted to the outside space at once, whereby it is possible to prevent the liquid discharged into the container 2 from being discharged to the outside space together with the gas.

In addition, according to the filtration device 1 according to the present embodiment, the plurality of vent holes 44a are provided at equal intervals. According to this configuration, for example, even in a case where the tubular portion 43 is unevenly disposed in a manner such that the gap CL is non-uniform with respect to the opening end portion 2B of the container 2, and the gap CL connected to any one vent hole 44a is closed, gas can be exhausted to the outside space through the other vent holes 44a. As a result, it is possible to more reliably suppress a decrease in the filtration efficiency of the filtration target object.

Further, according to the filtration device 1 according to the present embodiment, since the first housing portion 41 and the second housing portion 42 are made of resin, a total weight can be reduced as compared with a case where the first housing portion 41 and the second housing portion 42 are made of a metal such as lead. Thereby, it is possible to increase the extent of the use thereof. Additionally, even when the first housing portion 41 and the second housing portion 42 are made of resin and the weights are reduced, according to the filtration device 1 according to the present embodiment, the gas in the container 2 can be exhausted through the vent holes 44a, and thus, for example, it is possible to prevent the filtration device 1 from being detached from the container 2 due to an increase in the pressure in the container 2.

Note that the present invention is not limited to the above-described embodiment, and may be implemented in various other modes. For example, the filtration filter 3 is a metal filter in the above description, but the present invention is not limited thereto. The filtration filter 3 may be any filter capable of filtering the filtration target object contained in the liquid. For example, the filtration filter 3 may be another filter such as a membrane.

In addition, in the above description, the vent holes 44a are formed so as to extend to the outer side portion along the lower surface of the flange portion 44, but the present invention is not limited thereto. The vent holes 44a may be provided so as to allow the gap CL and the outside space to communicate with each other. For example, the vent holes 44a may also be provided so as to pass through the inside of the flange portion 44. Further, the cross-sectional shape of the groove is not limited to a rectangular shape, and may be, for example, a V-shape, a U-shape, a trapezoidal shape, or the like.

Figure 6:
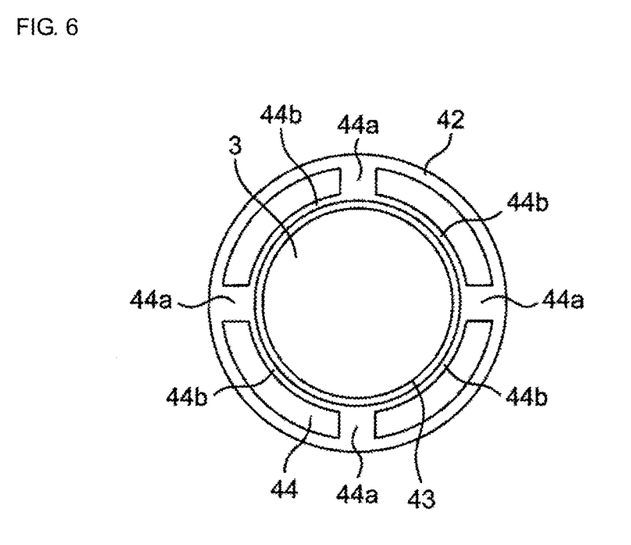
FIG. 6 is a bottom view illustrating a first modification of the filtration device illustrated in FIG. 1.
Figure 7:
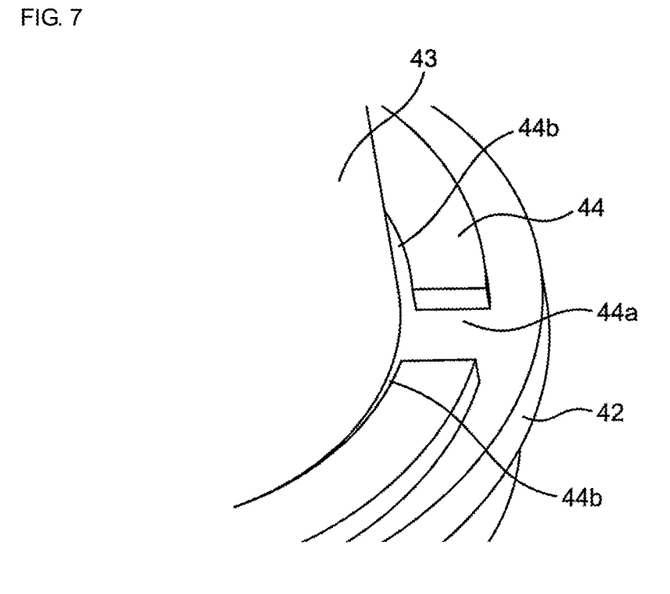
FIG. 7 is a partially enlarged perspective view of FIG. 6.

Additionally, in the above description, the plurality of vent holes 44a are provided independently of each other in the flange portion 44, however, the present invention is not limited thereto. For example, as illustrated in FIG. 6 and FIG. 7, the flange portion 44 may be provided with a communication hole 44b for communicating the plurality of vent holes 44a with each other. According to this configuration, for example, even in a case where any one of the plurality of vent holes 44a is clogged with foreign matters, it is possible to flow the gas into the other vent holes 44a through the communication hole 44b and to exhaust the gas from the other vent holes 44a to the outside space. As a result, it is possible to more reliably suppress a decrease in the filtration efficiency of the filtration target object.

Figure 8:
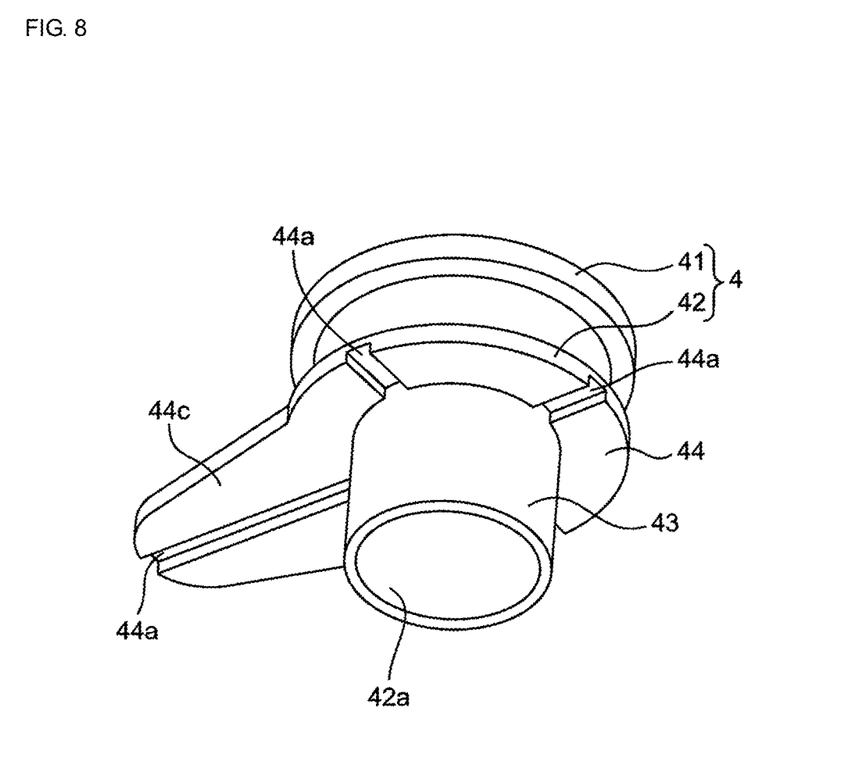
FIG. 8 is a bottom view illustrating a second modification of the filtration device illustrated in FIG. 1.

In addition, although the outer shape of the flange portion 44 is a circular shape in the above description, the present invention is not limited thereto. For example, as illustrated in FIG. 8, the flange portion 44 may include a handle portion 44c that extends further to the outer side portion than the other portions.

Note that the liquid containing a larger amount of the filtration target object than a capacity of the container 2 may erroneously flow through the filtration filter 3. In this case, the liquid that has passed through the filtration filter 3 may overflow from the inside of the container 2, and flow back to the filtration filter 3. For example, in a case where a medium containing cells is filtered by the filtration device 1, the cells isolated by the filtration filter 3 may be re-taken into the medium in which the cells are isolated and contaminated, because the medium becomes old. For this reason, in the state in which the tubular portion 43 of the housing 4 is inserted with a gap in the inner side portion with respect to the opening end portion 2B of the container 2, the filtration filter 3 is preferably provided so as to be positioned above the vent holes 44a, as illustrated in FIG. 3. Accordingly, it is possible to prevent the liquid that has passed through the filtration filter 3 from overflowing from the inside of the container 2 and flowing back to the filtration filter 3, and to prevent the cells from being contaminated by the old medium.

Figure 9:
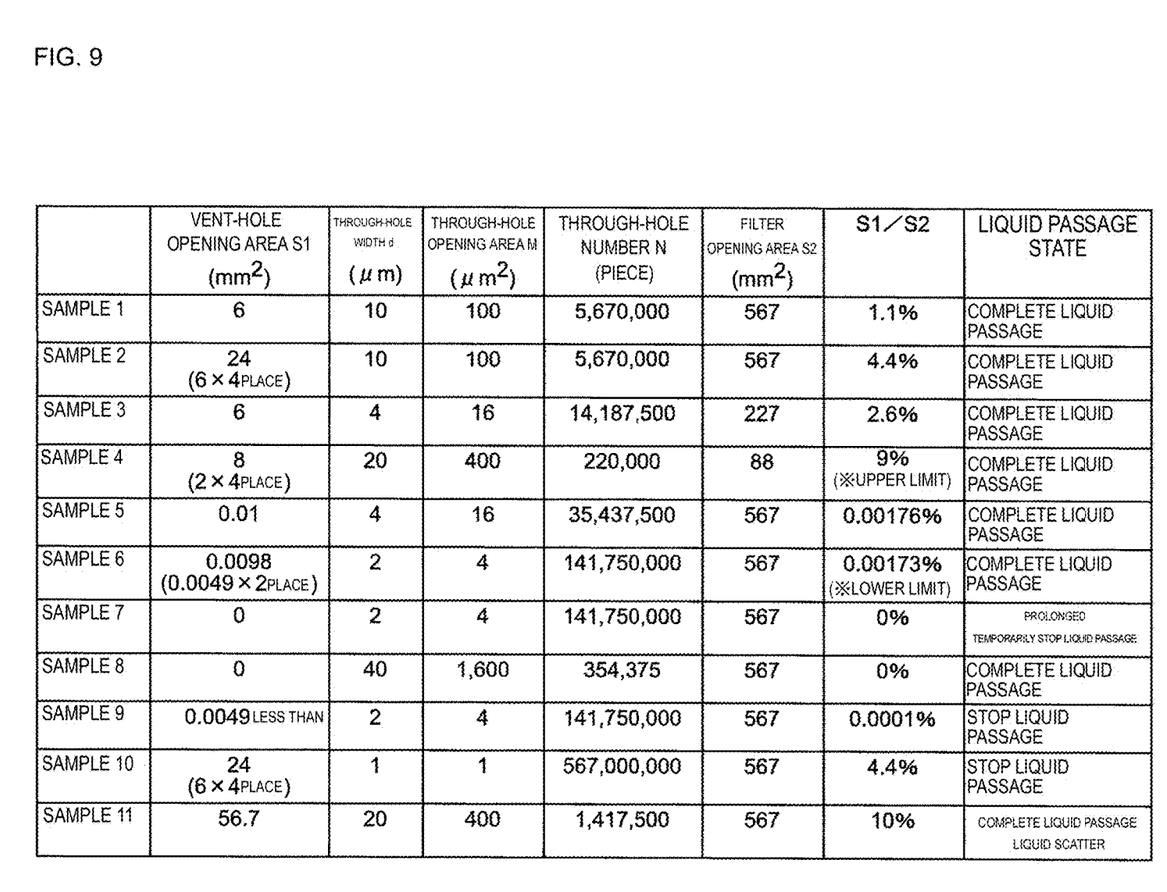
FIG. 9 is a table illustrating results of experiments performed by changing an opening area of a vent hole and an opening area of each through-hole of a filtration filter in the filtration device illustrated in FIG. 1.

Next, results of experiments performed for checking a preferred opening area of the vent hole 44a will be described. FIG. 9 is a figure illustrating the results of experiments performed by changing an opening area of the vent hole 44a and an opening area of each through-hole 31c of the filtration filter 3 in the filtration device 1.

Here, a beaker having a capacity of 750 ml was used as a container having a bottomed tubular shape. In addition, 500 ml of phosphate buffered saline (PBS) containing $1 \times 10^7$ cells HL-60 was used as a liquid containing a filtration target object. Further, as the filtration filter 3, 11 sheets of metal filters were prepared by changing the opening area of the vent hole 44a and the opening area of each through-hole 31c of the filtration filter 3, and 11 filtration devices including any one sheet of the metal filter were manufactured. Hereinafter, these filtration devices will be referred to as Sample 1 to Sample 11.

After that, Sample 1 was placed so as to cover an upper cavity of the beaker, and then the PBS was dropped onto an upper surface of the metal filter at once, and a liquid passing state was observed until the PBS passed through the metal filter to be contained in the beaker. This operation was repeated by changing the sample that is placed so as to cover the upper cavity of the beaker.

Note that in FIG. 9, an opening area S1 of the vent hole refers to a minimum opening area of the vent hole when one vent hole is provided, and refers to a total opening area obtained by adding the minimum opening area of each vent hole when a plurality of vent holes is provided. Further, the opening area S2 of the filtration filter refers to a total opening area of the plurality of through-holes provided in the filtration filter. The opening area S2 of the filtration filter can be calculated by integrating an opening area M of the through-hole and a number N of the through-holes. Here, for ease of description, the opening area M of each through-hole in one sample is assumed to be the same, and the shape of the through-hole in a plan view is assumed to be a square shape. Therefore, a width d of the through-hole refers to a length of one side of the through-hole. The opening area M of the through-hole is a square of the width d.

As illustrated in FIG. 9, in a case where filtration was performed using Sample 1 to Sample 6, liquid passage was completed, and good results were obtained.

On the other hand, when filtration was performed using Sample 7 having the same configuration as that of Sample 6 except that the vent hole was not provided, the liquid passage was not completed, and sometimes, the liquid passage was temporarily stopped. Further, when the upper surface of the metal filter was visually observed, bubbles were generated.

On the other hand, when the filtration was performed using Sample 8 having the same configuration as that of Sample 7 except that the opening area M of the through-hole was set to 1,600 μm², the liquid passage was completed, and good results were obtained. This is because the opening area M of the through-hole is large, and the gas in the beaker is exhausted through the through-hole to the outside space without providing a vent hole, and it is assumed that an increase in the pressure in the beaker is suppressed. That is, it is considered that the above-described effects can be obtained by providing the vent hole when the opening area M of the through-hole is less than 1,600 μm². In view of the results of filtering using Sample 4, it is considered that the above-described effects can be obtained when at least the opening area M of the through-hole is equal to or less than 400 μm².

Further, when the filtration was performed using Sample 9 having the same configuration as that of Sample 6 except that the opening area S1 of the vent hole was set to be less than 0.0049 mm², the liquid passage was stopped, and the filtration was not completed. This is presumably because the opening area S1 of the vent hole was too small, and thus the gas in the container 2 could not be sufficiently exhausted to the outside space. Accordingly, it is considered that the opening area S1 of the vent hole is preferably equal to or more than 0.0049 mm².

Further, when the filtration was performed using Sample 10 having the same configuration as that of Sample 2 (the opening areas S1 and S2 are the same) except the opening area M of the through-hole, the liquid passage was stopped, and the filtration was not completed. This is presumably because the opening area M of the through-hole was too small, and thus the PCB was unable to pass through the metal filter. Accordingly, it is considered that the opening area M of the through-hole is preferably equal to or more than 4 μm².

Further, when the filtration was performed by using Sample 11 in which the opening area M of the through-hole was made to be the same as that of Sample 4, while a ratio S1/S2 of the opening area S1 of the vent hole to the opening area S2 of the metal filter was set to 10%, which is higher than that of Sample 4, the liquid passage was completed. However, in this case, the liquid in the beaker was scattered to the outside space through the vent hole. Further, dust was mixed in the liquid in the beaker through the vent hole. Accordingly, it is considered that the ratio S1/S2 of the opening area S1 of the vent hole to the opening area S2 of the metal filter is preferably equal to or less than 9%.

That is, it is preferable that the opening area M of the through-hole 31c be 4 μm² to 400 μm², the opening area S1 of the vent hole be equal to or more than 0.0049 mm², and the ratio S1/S2 of the opening area S1 of the vent hole to the opening area S2 of the filtration filter be equal to or more than 0.00173%. According to this configuration, it is possible to prevent the vent hole from becoming excessively small, and to exhaust the gas in the container through the vent hole to the outside space more reliably. As a result, it is possible to more reliably suppress a decrease in the filtration efficiency of the filtration target object.

Further, it is preferable that the ratio S1/S2 of the opening area S1 of the vent hole to the opening area S2 of the filtration filter be equal to or less than 9.0%. According to this configuration, it is possible to suppress an excessive increase in the vent hole, and it is possible to prevent dust or the like from entering through the vent hole. Further, the gas in the container is exhausted to the outside space at once, whereby it is possible to prevent the liquid discharged into the container from being discharged to the outside space together with the gas.

Although the preferred embodiment according to the present invention has been described sufficiently in detail with reference to the accompanying drawings, it will be apparent to those skilled in the art that various changes and modifications may be made therein. It should be understood that such changes and modifications are included therein without departing from the scope of the invention as defined by the appended claims.

The present invention can improve the filtration efficiency of a filtration target object, and therefore is useful in a filtration device for filtering a filtration target object contained in a liquid such as biological products.

REFERENCE SIGNS LIST

1 FILTRATION DEVICE
2 CONTAINER
2A UPPER CAVITY
2B OPENING END PORTION
3 FILTRATION FILTER
4 HOUSING
31 FILTER PORTION
31a FIRST MAIN SURFACE
31b SECOND MAIN SURFACE
31c THROUGH-HOLE
32 FRAME PORTION
41 FIRST HOUSING PORTION
41a LIQUID INFLOW PATH
41b CONVEX STEP PORTION
42 SECOND HOUSING PORTION
42a LIQUID DISCHARGE PATH
42b CONCAVE STEP PORTION
43 TUBULAR PORTION
44 FLANGE PORTION
44a VENT HOLE
44b COMMUNICATION HOLE
44c HANDLE PORTION

The invention claimed is:

1. A filtration device comprising:
a filtration filter having a first main surface that captures a filtration target object contained in a liquid and a second main surface that faces the first main surface; and
a housing that holds the filtration filter, and defines a liquid inflow path that faces the first main surface and a liquid discharge path that faces the second main surface, the housing including:
a tubular portion that extends in a direction away from the second main surface of the filtration filter and defines at least a part of the liquid discharge path; and
a flange portion that extends from an outer peripheral surface of the tubular portion, the flange portion including at least one vent hole extending away from the outer peripheral surface of the tubular portion,
wherein the vent hole is a groove that extends to an outer side portion of the flange portion along a lower surface of the flange portion.

2. The filtration device according to claim 1, wherein the flange portion includes a plurality of the vent holes provided at intervals.

3. The filtration device according to claim 2, wherein the flange portion further includes a communication hole connecting the plurality of the vent holes to each other.

4. The filtration device according to claim 2, wherein the plurality of the vent holes are spaced at equal intervals.

5. The filtration device according to claim 4, wherein the flange portion further includes a communication hole connecting the plurality of the vent holes to each other.

6. The filtration device according to claim 1,
wherein the filtration filter has a plurality of through-holes penetrating from the first main surface to the second main surface,
an opening area of each of the plurality of through-holes is 3 $\mu m^2$ to 400 $\mu m^2$,
an opening area (S1) of the vent hole is equal to or more than 0.0049 $mm^2$, and
a ratio (S1/S2) of the opening area (S1) of the vent hole to an opening area (S2) of the filtration filter is equal to or more than 0.00173%.

7. The filtration device according to claim 6, wherein a ratio (S1/S2) of an opening area (S1) of the vent hole to an opening area (S2) of the filtration filter is equal to or less than 9.0%.

8. The filtration device according to claim 1, wherein the housing is made of resin.

9. The filtration device according to claim 1, wherein the housing further includes:
a first housing portion that defines the liquid inflow path; and
a second housing portion that includes the tubular portion, wherein
the first housing portion and the second housing portion are configured to fit with each other and hold the filtration filter between the first housing portion and the second housing portion.

10. The filtration device according to claim 1, wherein the first housing portion and the second housing portion hold an outer peripheral portion of the filtration filter therebetween.

11. The filtration device according to claim 1, wherein the housing holds the filtration filter in a position above the vent hole relative to the liquid inflow path.

12. The filtration filter according to claim 1, wherein the tubular portion is dimensioned so as to form a gap between the outer peripheral surface of the tubular portion and an inner side portion of an opening end of a bottomed tubular container when inserted into the opening end.

13. The filtration filter according to claim 12, wherein the vent hole is configured to communicate with the gap and an outside of the bottomed tubular container.

* * * * *